(12) United States Patent
Shin et al.

(10) Patent No.: US 7,576,214 B2
(45) Date of Patent: Aug. 18, 2009

(54) PROCESS FOR PREPARING 7-CHLORO-1-CYCLOPROPYL-6-FLUORO-4-OXO-1,4-DIHYDRO-1,8-NAPHTHYRIDINE-3-CARBOXYLIC ACID

(75) Inventors: Hyun-Ik Shin, Daejeon (KR); Jay-Hyok Chang, Daejeon (KR); Kyu-Woong Lee, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 496 days.

(21) Appl. No.: 10/572,636

(22) PCT Filed: Oct. 22, 2004

(86) PCT No.: PCT/KR2004/002705

§ 371 (c)(1),
(2), (4) Date: Mar. 17, 2006

(87) PCT Pub. No.: WO2005/040164

PCT Pub. Date: May 6, 2005

(65) Prior Publication Data

US 2007/0021613 A1 Jan. 25, 2007

(30) Foreign Application Priority Data

Oct. 29, 2003 (KR) ...... 10-2003-0075962

(51) Int. Cl.
*C07D 471/02* (2006.01)
*C07D 215/00* (2006.01)

(52) U.S. Cl. ...... 546/123; 546/156

(58) Field of Classification Search ...... 546/123, 546/156
See application file for complete search history.

(56) References Cited

U.S. PATENT DOCUMENTS 6,699,989 B1 * 3/2004 Shetty ...... 540/580

FOREIGN PATENT DOCUMENTS

| EP | 0 160 578 A1 | 11/1985 |
| JP | 3-74231 A | 3/1991 |
| JP | 2002-155081 A | 5/2002 |
| WO | WO-89/06649 A2 | 7/1989 |

OTHER PUBLICATIONS

DN 106:18399, Chu et al abstract (1986).*
DN 104:129888, Narita et al abstract (1985).*
DN 128:321632, Antons et al abstract (1997).*
Nishimura et al., 'An intramolecular cyclization of 7-substituted 6-fluoro-1,8-naphthyridine and -quinoline derivatives [1] [2]', J. Heterocyclic Chem. Mar.-Apr. 1988, vol. 25, pp. 479-485.
Sanchez et al., 'An efficient synthesis of 6-fluoronalidixic acid and its cinversion to enoxacin', J. Heterocyclic Chem. Jan.-Feb. 1987, vol. 24, pp. 215-217.
Egawa et al., 'Pyridonecarboxylic acids as antibacterial agents. 4. Synthesis and antibacterial activity of 7-(3-amino-1-pyrrolidinyl)-1-ethyl-6-fluoro-1,4-dihydro-4-oxo-1,8-naphthyridine-3-carboxylic acid and its analogues', J. Med. Chem., 1984, vol. 27, pp. 1543-1548.
Matsumoto et al., 'Pyridonecarboxylic acids as antibacterial agents. 2. Synthesis and structure-activity relationships of 1,6,7-trisubstituted 1,4-dihydro-4-oxo-1,8-naphthyridine-3-carboxylic acids, including enoxacin, a new antibacterial agent', J. Med. Chem.

* cited by examiner

*Primary Examiner*—Janet L. Andres
*Assistant Examiner*—Raymond Covington
(74) *Attorney, Agent, or Firm*—Birch, Stewart, Kolasch & Birch, LLP

(57) ABSTRACT

Starting from ethyl 3-(2,6-dichloro-5-fluoropyridin-3-yl)-3-oxo-propanoate (1), the present invention provides highly pure 7-chloro-1-cyclopropyl-6-fluoro-4-oxo-1,4-dihydro-1,8-naphthyridine-3-carboxylic acid (5) in one-pot four steps using a single solvent.

10 Claims, No Drawings

PROCESS FOR PREPARING 7-CHLORO-1-CYCLOPROPYL-6-FLUORO-4-OXO-1,4-DIHYDRO-1,8-NAPHTHYRIDINE-3-CARBOXYLIC ACID

TECHNICAL FIELD

The present invention relates to a novel process for preparing 7-chloro-1-cyclopropyl-6-fluoro-4-oxo-1,4dihydro-1,8-naphthyridine-3-carboxylic acid. Starting from ethyl 3-(2,6-dichloro-5-fluoropyridin-3-yl)-3-oxo-propanoate (1), the present invention provides highly pure 7-chloro-1-cyclopropyl-6-fluoro-4-oxo-1,4-dihydro-1,8-naphthyridine-3-carboxylic acid (5)using single solvent in one-pot manner as shown in Scheme 1.

Reaction Scheme 1

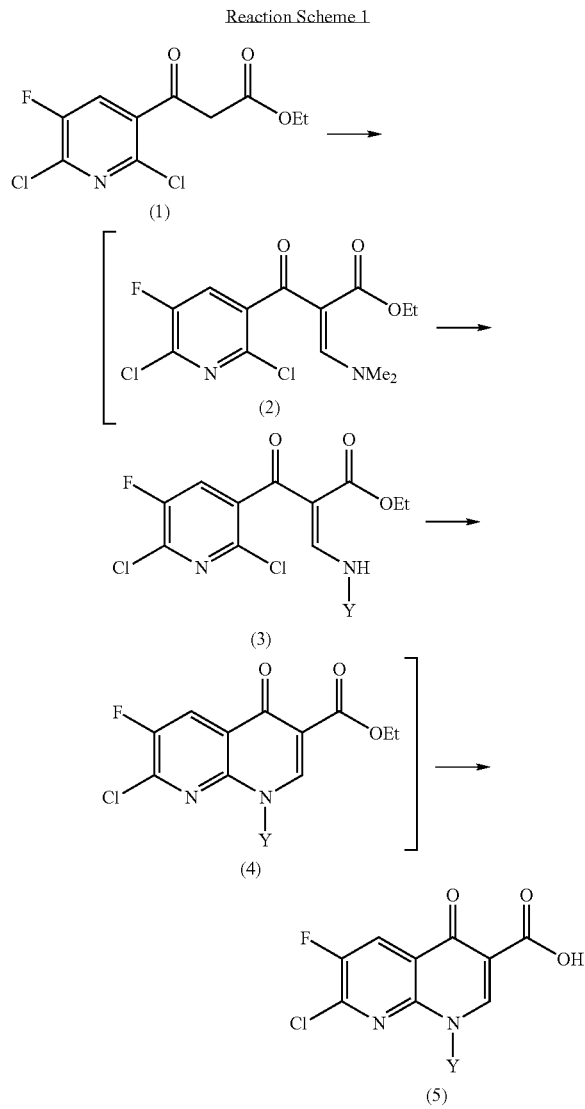

in which

Y represents straight-chain, branched, or cyclic alkyl, having 1 to 5 carbon atoms, and unsubstituted or substituted by halogen, or represents phenyl unsubstituted or substituted by halogen.

BACKGROUND ART

Efficient preparation of compound (5) of the above Reaction Scheme 1 is critical for an economical production of a fluoroquinolone-based antibiotic used for the treatment of microbial infection. A prior process known in JP Laid-Open Hei 3-74231 prepares compound (5) through the following three steps:

Step 1: 3-(2,6-Dichloro-5-fluoropyridin-3-yl)-3-oxopropanoic acid ethyl ester is reacted with triethyl orthoformate and acetic anhydride to prepare 2-[(2,6-dichloro-5-fluoropyridin-3-yl)carbonyl]-3-ethoxy acrylic acid ethyl ester;

Step 2: thus obtained compound is reacted with cyclopropylamine, and

Step 3: the resulting cyclopropyl enamine is cyclized by sodium hydride to prepare naphthyridine ester.

However, in this process, the intermediates are separated at each step, and so the whole operation is complicated and resulted in low yield.

Another process to prepare compound (5) has been described in JP Laid-Open 2002-155081. This process improves the above process described in JP Laid-Open Hei 3-74231 which is carried out the above steps 1 to 3 in the same solvent without any intermediate isolation process. This invention may be illustrated in more detail in the following three steps:

Step 1: Compound (1) is reacted with triethyl orthoformate by heating in the presence of acetic anhydride with concomitant removal of the by-products, ethanol and acetic acid. After the completion of the reaction, the residual triethyl orthoformate should be completely distilled off under reduced pressure to prevent the formation of side product in the next step.

Step 2: Thus obtained residue is cooled and dissolved in toluene. To this solution is added dropwise cyclopropylamine to prepare the enamine compound.

Step 3: Finally, a catalytic amount of tetrabutylammonium bromide is added to the solution of the enamine compound, and then aqueous sodium hydroxide solution is added to cyclize. The crystallized naphthyridine 3-carboxylic ester is filtered, washed, and dried and subsequently hydrolyzed to give compound (5) in the overall yield of about 85%.

This process is advantageous in preparing the naphthyridine ester without intermediates isolation, but also has the following disadvantage.

The reaction of Step 1 is already known in a number of references, and is a widely used as a general method (cf: WO 89/06649, EP 0 160 578 A1). However, this step has a couple of problems in an industrial aspect. First, after completion of the reaction, triethyl orthobromate should be removed thoroughly through distillation under reduced pressure. This process takes a long time. Second, if the triethyl orthoformate is not completely removed, the residual triethyl orthoformate reacts with cyclopropylamine introduced in the next step to form by-products that is difficult to purify.

DISCLOSURE OF THE INVENTION

The present inventors have conducted extensive studies to solve the problems in the above JP Laid-Open 2002-155081. As a result, we have found out that the object compound of the present invention, 1,8-naphthyridine-3-carboxylic acid derivative, can be prepared in high yield and purity in a short cycle time without any need to conduct complicated operations simply using dimethylformamide dialkylacetal instead of triethyl orthoformate at the first step. Accordingly, the preparation of intermediates of (2), (3)and (4)is proceeded in one-pot manner using the same solvent without any intermediate isolation process.

Below, the present invention is illustrated in more detail.

BEST MODE FOR CARRYING OUT THE INVENTION

The present invention relates to a process for preparing 1,8-naphthyridine-3-carboxylic acid derivative of the following formula (5) featuring one-pot operation using a single solvent without any intermediate isolation:

a) in the first step, the compound of the following formula (1)

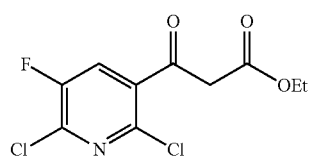
(1)

is reacted with dimethylformamide dialkylacetal of formula $Me_2NCH(OR)_2$ (wherein R represents straight-chain, branched or cyclic alkyl having 1 to 9 carbon atoms, or benzyl) in a solvent in the presence of acid catalyst to prepare the compound of the following formula (2),

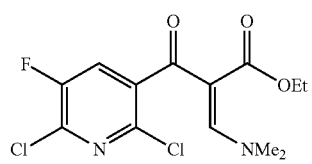
(2)

b) in the second step, the resulting compound of the following formula (2)

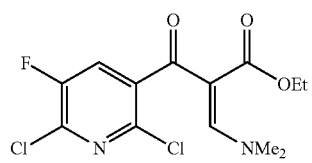
(2)

is reacted with amine of formula $YNH_2$ prepare the compound of the following formula (3),

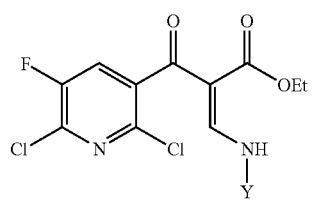
(3)

in which

Y represents straight-chain, branched or cyclic alkyl, having 1 to 5 carbon atoms and unsubstituted or substituted by halogen, or phenyl unsubstituted or substituted by halogen, c) in the third step, the resulting compound of the following formula (3),

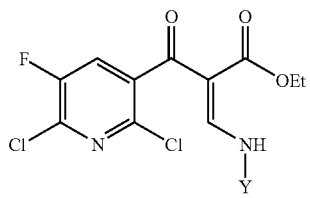
(3)

in which

Y is as defined above, is cyclized in the presence of quaternary ammonium salt and a base to prepare 1,8-naphthyridine-3-carboxylic acid ester of the following formula (4),

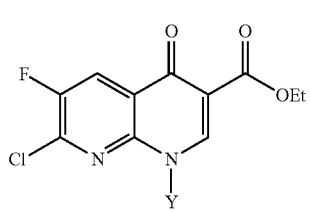
(4)

in which

Y is as defined above, and d) in the fourth step, the resulting compound of the following formula (4),

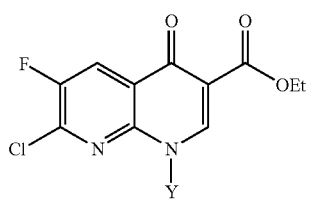
(4)

in which

Y is as defined above, is hydrolyzed in the presence of acid to prepare 1,8-naphthyridine-3-carboxylic acid derivative of the following formula (5),

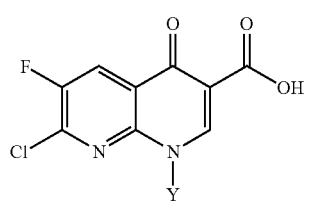
(5)

in which

Y is as defined above.

Each step above is illustrated in more detail as follows.

Process a)

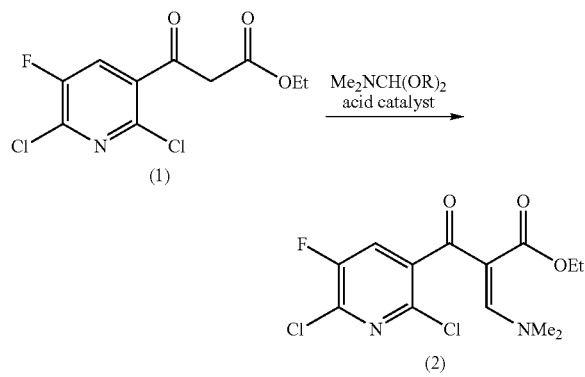

First, the solvent used in the processes a) to d) is halogenated alkane or aromatic hydrocarbon solvent. The examples of halogenated alkane solvents are methylene chloride, 1,2-dichloroethane, etc. The examples of aromatic hydrocarbon solvents are benzene, chlorobenzene, 1,2-dichlorobenzene, toluene, xylene, etc., preferably 1,2-dichlorobenzene or toluene. The solvent is used in the amount of 3 to 15 times (v/w), preferably 4 to 10 times (v/w), and more preferably 6 times (v/w) with respect to the compound (1).

The specific examples of R in dimethylformamide dialkylacetal [Me$_2$NCH(OR)$_2$] used as a reaction substance are methyl, ethyl, propyl, isopropyl, butyl, t-butyl, neopentyl, benzyl, cyclohexyl, etc., preferably methyl, ethyl, isopropyl, etc., and more preferably methyl. Dimethylformamide dialkylacetal is used in 1 to 3 mole equivalents, preferably 1 to 1.5 mole equivalents, and more preferably 1.05 to 1.15 mole equivalents per mole of the compound (1).

The examples of acid catalyst are organic carboxylic acids such as acetic, propionic, and butanoic acid, etc., preferably acetic acid. Among these, acetic acid is used in the amount of 0.05 to 0.6 mole equivalents, preferably 0.1 to 0.4 mole equivalents, more preferably 0.2 to 0.3 mole equivalents, per mole of the compound (1).

In the process a), the compound (1), dimethylformamide dialkylacetal, acid catalyst, and solvent may be combined in any order for the convenience of process because the combining order does not affect the reaction. The reaction temperature is between 0 and 50° C., preferably between 10° C. and 40° C., and more preferably between 20° C. and 30° C.

More specifically, the process a) according to the present invention is most preferably carried out by reacting compound (1) with 1.05 to 1.15 mole equivalents of dimethylformamide dimethylacetal and 0.2 to 0.3 mole equivalents of acetic acid in 6 times (v/w) of toluene with respect to compound (1) at 20° C. to 30° C.

Enamine structure shown in the compound (2) formed through process a) may be present in the mixture of E/Z form, and the present invention includes both forms.

Process b)

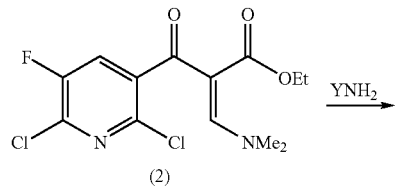

-continued

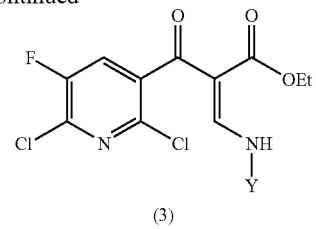

Amine of formula YNH$_2$ is added to the crude reaction mixture of compound (2) prepared according to process a). Here, specific examples of Y are such substituted or unsubstituted alkyl as methyl, ethyl, propyl, isopropyl, butyl, sec-butyl, t-butyl, pentyl, etc. Among these, straight-chain or branched alkyl having 1 to 4 carbons are preferred, and methyl, ethyl, and propyl are more preferred. In the case of halogen-substituted alkyl group, fluorine, chlorine, bromine, iodine, etc. may be incorporated as a halogen moiety, and among these, fluorine and chlorine are preferred. Specific examples of halogen-substituted alkyl group are chloromethyl, 2-chloroethyl, fluoromethyl, 1-fluoroethyl, 2-fluoroethyl, etc., among which fluoromethyl and 2-fluoroethyl are preferred. As examples of cyclic alkyl, there are cyclopropyl, cyclobutyl, cyclopentyl, cyclohexyl, etc. These cyclic alkyls may be substituted with halogen such as fluorine, chlorine, bromine, and iodine, preferably chlorine and fluorine, in any position. As preferable examples of cyclic alkyl, 2-fluorocyclopropyl, 2,2-difluorocyclopropyl, 2-chloro-2-fluorocyclopropyl, etc. may be mentioned, and as more preferable examples of cyclic alkyl, there are cyclopropyl or 2-chloro-2-fluorocyclopropyl, etc. Furthermore, specific examples of phenyl unsubstituted or substituted with halogen are phenyl, and 2,4-difluorophenyl, preferably 2,4-dufluorophenyl. In the present invention, cyclopropyl is most preferred.

In preparing the compound of formula (3) by using the above amine, amine of formula YNH$_2$ is used by 0.9 to 2 mole equivalents, preferably 1.0 to 1.5 mole equivalents, more preferably 1.1 to 1.3 mole equivalents, most preferably 1.1 to 1.2 mole equivalents, per mole of the compound (1). In this reaction, for the convenience of stirred mixing, same solvent may be added to the reaction solution through the whole steps, and the amount of solvent is 0 to 5 times (v/w) to the compound (1), but it is most advantageous not to add solvent in view of reaction speed and reaction volume. Here, the reaction temperature is between 0 and 50° C., preferably between 10° C. and 40° C., and more preferably between 20° C. and 30° C.

The solution containing the compound of formula (3) obtained in the above reaction includes alcohol formed as by-products, residual unreacted YNH$_2$, and dimethylamine liberated from the compound of formula (2). Thus, it is preferred that these by-products and unreacted substances be removed. In that context, washing with a diluted aqueous acid solution is employed to lead to the removal of amine derivatives as their salts form into the aqueous layer. The aqueous acid solution used therein may be prepared from inorganic acid such as diluted sulfuric acid, diluted hydrochloric acid, diluted phosphoric acid, or potassium hydrogen sulfate, etc., or organic acid such as tartaric acid, citric acid, etc. The pH during the washing is 1 to 6, preferably 2 to 5, more preferably 3 to 4. As an acid for washing, organic acids such as tartaric acid, citric acid, etc. are more preferred. Among them, citric acid is the most preferred. When citric acid is used, a preferable concentration of the aqueous solution is 3 to 30%, more preferably 5 to 20%, and still more preferably 10 to 15%. The washing temperature is between 10° C. and 50° C., preferably between 25° C. and 45° C., and more preferably between 30° C. and 40° C. The washing frequency may be one or several times, but if a preferable concentration of above citric acid is used at suitable temperature, one time of washing is sufficient. After layer separation, the separated organic layer may be washed one more time with neutral water, if necessary.

Process c)

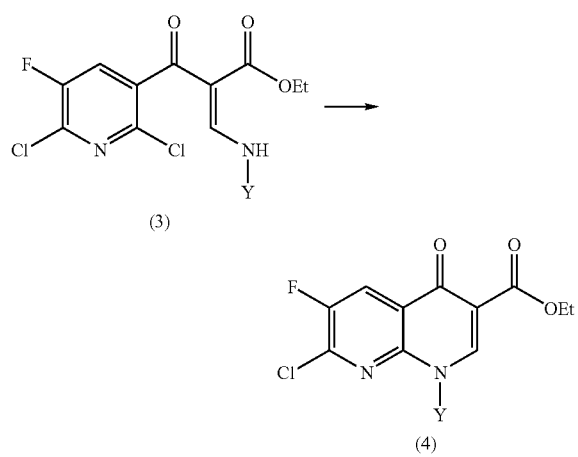

The crude compound (3) in the separated organic layer obtained in the process b) is cyclized in the presence of quaternary ammonium salt and a base to provide the compound of formula (4).

R in the quaternary ammonium salt ($R_4NX$) used in this process represents straight-chian or branched alkyl having 1 to 18 carbons, or benzyl, etc; four Rs may be same or different; and X represents halogen, $HSO_4^-$, or hydroxyl radical, wherein halogen is chlorine, bromine, iodine, etc. As quaternary ammonium salt in this process c) according to the present invention, benzyltrialkylammonium salt, tetramethylammonium salt, tetraethylammonium salt, tetrabutylammonium salt, or the trade name "Aliquat 336," "Adogen 464," etc. may be generally used. Preferably, benzyltriethylammonium chloride; or bromide, or iodide, or tetraethylammonium chloride; or bromide or iodide, or tetrabutylammonium chloride; or bromide or iodide is used. More preferably, tetrabutylammonium bromide is used. However, for convenience sake, any of the above mentioned kinds of quaternary ammonium salt may be used. The quaternary ammonium salt may be used in the form of solid or aqueous solution, and the used amount is 0.001 to 1 mole equivalents, preferably 0.01 to 0.1 mole equivalents, more preferably 0.03 to 0.05 mole equivalents, per mole of the compound (1).

If X in the quaternary ammonium salt ($R_4NX$) used herein is halogen or $HSO_4^-$, the use of base is essential, whereas when X is hydroxyl, quaternary ammonium salt itself functions as base, and so the use of extra base is optional. The kinds of usable base are aqueous solutions of lithium hydroxide, sodium hydroxide, potassium hydroxide, lithium carbonate, sodium carbonate, sodium hydrogen carbonate, potassium hydrogen carbonate, quaternary ammonium hydroxide, etc; preferably sodium hydroxide or potassium hydroxide. Among them, sodium hydroxide is the most preferable. The used amount of base in this process is 0.9 to 1.5 mole equivalents, preferably 1.0 to 1.3 mole equivalents, more preferably 1.1 to 1.2 mole equivalents, per mole of compound (1).

On the other hand, aqueous quaternary ammonium hydroxide solution may be used instead of the mixture of quaternary ammonium salt and base, and in this case, the aqueous quaternary ammonium hydroxide solution may be used in the amount of 0.9 to 1.5 mole equivalents, preferably 1.0 to 1.3 mole equivalents, more preferably 1.05 to 1.15 mole equivalents, per mole of compound (1). The reaction temperature is between 10 and 60° C., preferably between 20 and 50° C., more preferably between 25 and 35° C. In conclusion, the cyclization of intermediate (3) to (4) is accomplished in short time at ambient temperature to provide higher productivity as well as purity with respect to the known arts.

Process d)

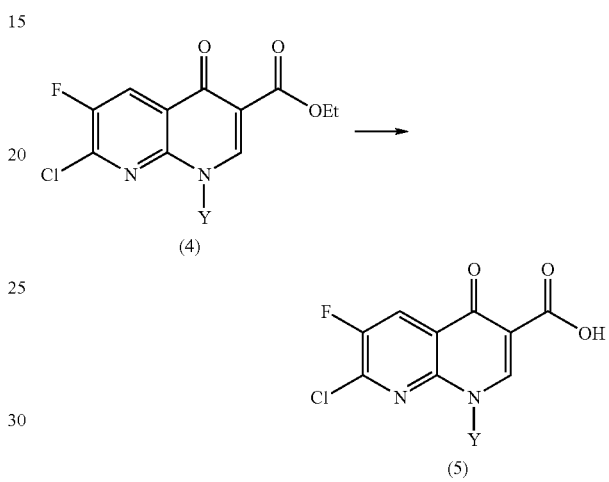

To the reaction mixture containing compound (4) prepared in process c) is added aqueous acid solution, and the mixture is heated for hydrolysis of the ester group, and the formed crystal is filtered to give compound (5).

The kind of acid used for hydrolysis is hydrochloric acid or sulfuric acid, preferably concentrated hydrochloric acid. The used amount is 1.5 to 9 mole equivalents, preferably 3 to 6 mole equivalents, more preferably 4 to 5 mole equivalents, per mole of compound (1). In particular, in case of using hydrochloric acid, 10 to 35% of aqueous hydrochloric acid solution may be used. It is preferred to use 35% of aqueous hydrochloric acid solution.

The reaction may be carried out at a temperature between room temperature and 120° C., preferably 60° C. and 120° C., more preferably 110° C. and 120° C. After the reaction is completed, the reaction solution is cooled, the resulting solid is filtered, washed with water and organic solvent, and the resulting filter cake is dried to give compound (5) in high purity. The overall yield over four stps is usually 90% or more.

As illustrated in the above description, the present invention has the following advantages: the whole steps are carried out in one pot manner without isolating the intermediates formed in each step and without any change or addition of solvent. Since operations such as isolation, solvent exchange, reactor change, and reactor washing, etc. are not required, the present invention provides compound (5) in a highly efficient and simple fashion in terms of cycle time of the process and the yield and quality of the product.

The following examples are presented to illustrate further the present invention. However, it should be understood that these examples are intended to illustrate the present invention, and cannot limit the scope of the present invention in any way.

EXAMPLE 1

Preparation of 7-Chloro-1-cyclopropyl-6-fluoro-4-oxo-1,4-dihydro-1,8-naphthyridine-3-carboxylic acid [using tetrabutylammonium hydroxide]

To a stirred solution of 3-(2,6-Dichloro-5-fluoropyridin-3-yl)-3-oxo-propanoic acid ethyl ester (compound (1): 10.0 g, 35.7 mmol) in toluene (60 ml) was added dimethyl-formamide dimethylacetal (4.68 g, 39.3 mmol) and acetic acid (0.53 g, 8.9 mmol) at room temperature. The mixture was stirred at room temperature for 30 minutes. After 3-(2,6-dichloro-5-fluoropyridin-3-yl)-3-oxo-propanoic acid ethyl ester [compound (1)] was completely disappeared (monitored by HPLC), cyclopropylamine (2.24 g, 39.3 mmol) was added thereto, and the mixture was stirred for 30 minutes. After compound (2) was completely disappeared (monitored by HPLC), the reaction mixture was washed with 10% aqueous citric acid solution. After layer separation, the separated organic layer was washed with distilled water, and 25% aqueous tetrabutylammonium hydroxide solution (40 g, 39.3 mmol) was added to the solution. The resulting solution was stirred for 1 hour. After compound (3) was completely disappeared (monitored by HPLC), concentrated hydrochloric acid (14.7 ml, 146 mmol) was added to the reaction solution, and the mixture was heated under reflux for 10 hours. The reaction solution was cooled, filtered, washed with isopropanol, distilled water, and isopropanol in turn, and dried to give the title compound (5) (9.4 g) as a white crystal.

Total yield: 93.1%
Purity (HPLC): 98.6%.

EXAMPLE 2

Preparation of 7-Chloro-1-cyclopropyl-6-fluoro-4-oxo-1,4-dihydro-1,8-naphthyridine-3-carboxylic acid [using tetrabutylammonium hydroxide and sodium hydroxide]

Starting from 3-(2,6-Dichloro-5-fluoropyridin-3-yl)3-oxo-propanoic acid ethyl ester (compound (1): 10.0 g, 35.7 mmol) in toluene (70 ml), compound (3) was prepared according to the same procedure as Example 1. To the separated toluene solution of compound (3) was added distilled water (10 ml) and then 40% aqueous tetrabutylammonium hydroxide solution (2.32 g, 3.57 mmol) and 10N sodium hydroxide (3.93 ml, 39.3 mmol) were added thereto to cyclize the reaction solution. After 1.3 hours, concentrated hydrochloric acid (16.7 ml) was added to the reaction solution, and the mixture was heated under reflux for 8 hours to hydrolyze the mixture. The reaction solution was cooled, and the resulting solid was filtered, washed according to the same procedure as Example 1, and dried to give the title compound (5) (9.3 g) as a white crystal.

Total yield: 92.1%
Purity (HPLC): 99.9%.

EXAMPLE 3

Preparation of 7-Chloro-1-cyclopropyl-6-fluoro-4-oxo-1,4-dihydro-1,8-naphthyridine-3-carboxylic acid To a stirred solution of 3-(2,6-Dichloro-5-fluoropyridin-3-yl)-3-oxo-propanoic acid ethyl ester (compound (1): 85.0 kg, 303 mol) in toluene (808 kg) was added Me$_2$NCH(OMe)$_2$ (40.8 kg) and acetic acid (4.56 kg). The mixture was stirred at room temperature for 50 minutes. Cyclopropylamine (22.53 kg) was added to the reaction mixture, and the mixture was stirred at 25 to 35° C. for 50 minutes. The reaction mixture was washed with 10% aqueous citric acid solution, and then water. After layer separation, the aqueous layer was discarded, and tetrabutylammonium bromide (4.88 kg) and 25% aqueous sodium hydroxide solution (53 kg) were added to the separated organic layer. The resulting mixture was stirred for 2 hours. 35% aqueous hydrochloric acid solution (142 kg) was added, and the resulting mixture was heated at reflux. After about 8 hours, the reaction mixture was cooled, and water (about 50 kg) was added thereto, and then the aqueous layer was separated off. The reaction solution was washed with water, and the solid compound present in the separated organic layer was filtered, and washed with isopropanol, water, and isopropanol in sequence. The resulting solid was dried under vacuum to give the title compound (77 kg) as a white crystal.

Total yield: 90%
Purity (HPLC): 99.9%.

The invention claimed is:
1. A process for preparing 1,8-naphthyridine-3-carboxylic acid compound of the following formula (5)

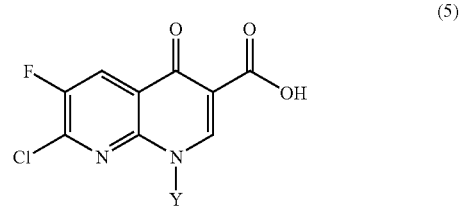

in which
Y represents straight-chain, branched or cyclic alkyl, having 1 to 5 carbon atoms, and unsubstituted or substituted by halogen, said process comprising:
the first step a) the compound of the following formula (1),

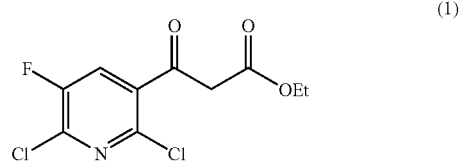

is reacted with dimethylformamide dialkylacetal of formula Me$_2$NCH(OR)$_2$ (wherein R represents straight-chain, branched or cyclic alkyl having 1 to 9 carbon atoms, or represents benzyl) in a solvent in the presence of acid catalyst to prepare the compound of the following formula (2),

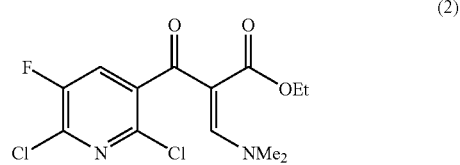

the second step b) the resulting reaction mixture of the following formula (2),

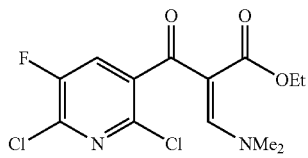
(2)

is reacted with amine of formula YNH$_2$ to prepare the compound of the following formula (3),

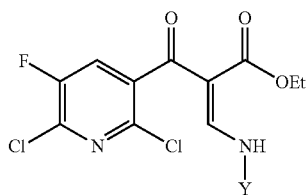
(3)

in which
Y is defined as above,
the third step c) the resulting compound of the following formula (3),

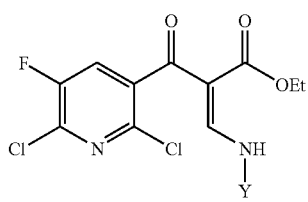
(3)

in which
Y is as defined above,
is cyclized in the presence of quaternary ammonium salt and a base to prepare 1,8-naphthyridine-3-carboxylic acid ester of the following formula (4),

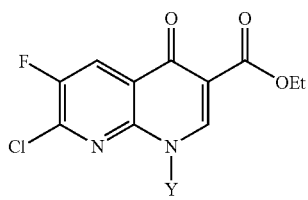
(4)

in which
Y is as defined above, and
in the fourth step d) the resulting compound of the following formula (4),

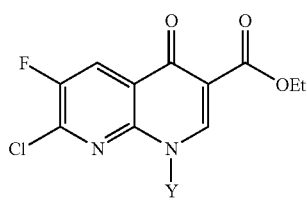
(4)

in which
Y is as defined above,
is hydrolyzed in the presence of an acid to prepare 1,8-naphthyridine-3-carboxylic acid compound of the said formula (5),
said process is characterized by a one pot operation of the above steps using a single solvent system without intermediate isolation.

2. The process according to claim 1 wherein R represents methyl.

3. The process according to claim 1 wherein the solvent used is toluene.

4. The process according to claim 1 wherein dimethylformamide dialkylacetal of formula [Me$_2$NCH(OR)$_2$] is employed from 1.05 to 1.15 mole equivalents per mole of the compound of formula (1).

5. The process according to claim 1 wherein in the step a), acetic acid as acid catalyst is employed from 0.2 to 0.3 mole equivalents per mole of the compound of formula (1).

6. The process according to claim 1 wherein amine of formula YNH$_2$ is cyclopropylamine.

7. The process according to claim 1 wherein amine of formula YNH$_2$ is employed from 1.1 to 1.2 mole equivalents per mole of the compound of formula (1).

8. The process according to claim 1 wherein the reaction solution after the step b) is washed with aqueous citric acid solution.

9. The process according to claim 1 wherein in the step c), aqueous tetrabutylammonium hydroxide solution is used as base.

10. The process according to claim 1 wherein in the step d), the reaction solution is heated under reflux by using concentrated aqueous hydrochloric acid.

* * * * *

UNITED STATES PATENT AND TRADEMARK OFFICE
CERTIFICATE OF CORRECTION

PATENT NO. : 7,576,214 B2  Page 1 of 1
APPLICATION NO. : 10/572636
DATED : August 18, 2009
INVENTOR(S) : Hyun-Ik Shin et al.

It is certified that error appears in the above-identified patent and that said Letters Patent is hereby corrected as shown below:

In the Claims:

In claim 1, column 10, line 39, "by halogen, said process comprising"

should read

--by halogen, or represents phenyl unsubstituted or substituted by halogen, said process--.

Signed and Sealed this

Nineteenth Day of January, 2010

David J. Kappos
*Director of the United States Patent and Trademark Office*